US00PP30999P3

(12) United States Plant Patent
Bierhuizen

(10) Patent No.: US PP30,999 P3
(45) Date of Patent: Oct. 29, 2019

(54) ***LAVANDULA* PLANT NAMED 'LA007'**

(50) Latin Name: *Lavandula angustifolia*
Varietal Denomination: LA007

(71) Applicant: Sunrise Greenhouses Ltd., Vineland (CA)

(72) Inventor: Rodney Bierhuizen, Vineland (CA)

(73) Assignee: SUNRISE GREENHOUSES LTD., Vineland, Ontario (CA)

( * ) Notice: Subject to any disclaimer, the term of this patent is extended or adjusted under 35 U.S.C. 154(b) by 0 days.

(21) Appl. No.: 16/350,257

(22) Filed: Oct. 19, 2018

(65) Prior Publication Data

US 2019/0124815 P1 Apr. 25, 2019

(30) Foreign Application Priority Data

Oct. 23, 2017 (CA) ..... PBR 17-9324

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./263.1, 445
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Lavandula* plant, 'LA007' that is characterized by its foliage that is silver in color, its flowers that are light purple in color, its pyramidal upright growth habit, and its well-branched plant habit.

2 Drawing Sheets

Botanical classification: *Lavandula angustifolia.*
Variety denomination: 'LA007'.

BACKGROUND OF THE INVENTION

The present invention relates to a new and distinct cultivar of *Lavandula angustifolia* and will be referred to hereafter by its cultivar name, 'LA007'. 'LA007' is a new variety of English lavender suitable for container use.

The new cultivar was discovered as a branch mutation by the Inventor in May of 2015 in Vineland, Ontario, Canada. The new cultivar arose as a naturally occurring branch mutation of *Lavandula angustifolia* 'LA006' (unreleased proprietary plant discovered by the Inventor, not patented,) that was growing in a container at a nursery. The parent plant, 'LA006', is a mutation of *Lavandula angustifolia* 'Munstead' (not patented).

Asexual propagation of the new cultivar was first accomplished by the inventor by stem cuttings in June of 2015 in Vineland, Ontario, Canada. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'LA007' as a unique cultivar of *Lavandula.*

1. 'LA007' exhibits foliage that is silver in color.
2. 'LA007' exhibits flowers that are light purple in color.
3. 'LA007' exhibits a pyramidal upright growth habit.
4. 'LA007' exhibits a well-branched plant habit.

The parent plant of 'LA007', 'LA006', is similar to 'LA007' in having a pyramidal upright growth habit and a well-branched plant habit. 'LA006' differs from 'LA007' in having foliage that is green in color and flower buds that are purple in color and do not open. 'LA007' can also be closely compared to the cultivar 'Munstead'. 'Munstead' differs from 'LA007' in having foliage that is dull grey in color, blue flowers, and a mounded compact growth habit.

BRIEF DESCRIPTION OF THE DRAWINGS

The accompanying colored photographs illustrate the overall appearance and distinct characteristics of one year-old plants of the new *Lavandula* as grown outdoors in 14-cm containers in 2018 in St. Thomas, Canada.

The photograph in FIG. 1 illustrates the overall plant habit of 'LA007' in spring.

Figure 1:
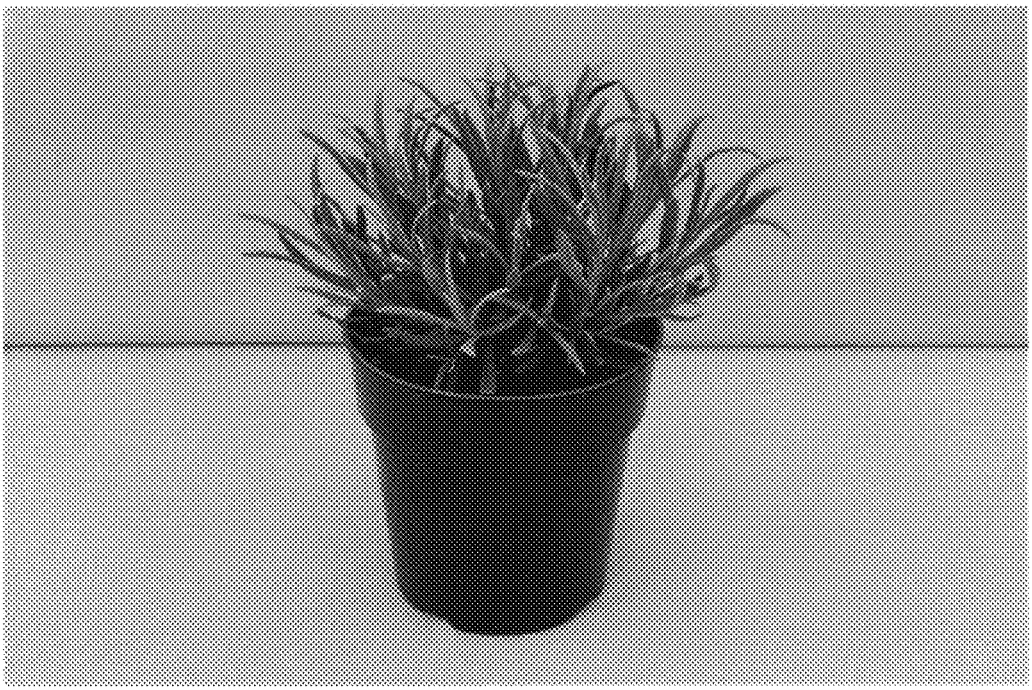
Figure 2:
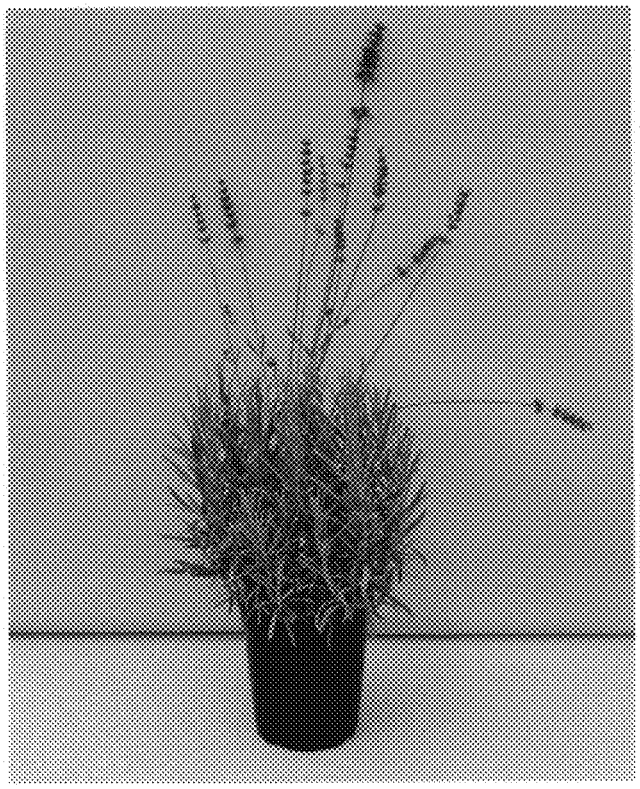

The photograph in FIG. 2 illustrates the plant habit in summer.

Figure 3:
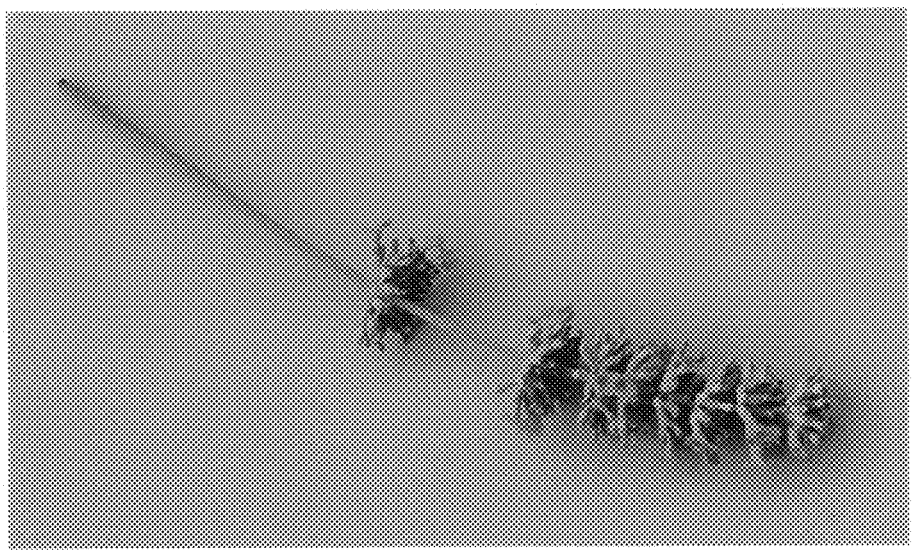

The photograph in FIG. 3. provides a close up view of an inflorescence of 'LA007'.

The colors in the photographs are as close as possible with the digital photography techniques utilized and the color values cited in the detailed botanical description accurately describe the colors of the new *Lavandula.*

DETAILED BOTANICAL DESCRIPTION

The following is a detailed description of one year-old plants of the new cultivar as grown outdoors in 14-cm containers in St. Thomas, Canada. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General description:

*Blooming habit.*—Blooms from early to late summer in Vineland, Ontario, Canada.

*Plant type.*—Perennial, subshrub.

*Plant habit.*—Upright and pyrimidal.

*Height and spread.*—Reaches about 40.2 cm in height and 29.9 cm in spread in a 14-cm container.

*Cold hardiness.*—At least in U.S.D.A. Zone 7b.

*Diseases and pests.*—Not more susceptible or resistant to pests and diseases than other *Lavandula.*

*Root description.*—Densely fibrous, freely branched, vigorously formed during propagation, typically 155A in color.

*Root development.*—Plants can be finished in a 14-cm container in 32 weeks from a rooted cutting.

*Propagation.*—Terminal stem cuttings.

*Growth.*—Medium vigour for a *Lavandula angustifolia* cultivar.

Stem description:

*Stem shape.*—Square.

*Stem color.*—Young; ranging between 157A to 157B, mature wood; 200D.

*Stem surface.*—Dull and very densely tomentose hairs about 0.2 mm in length and NN155D in color.

*Stem size.*—Average of 28.9 cm in length and 3.5 mm in diameter.

*Stem strength.*—Strong.

*Stem aspect.*—Upright.

*Branching.*—Approximately 18 basal branches on one-year old plants grown in 14 cm containers.

Foliage description:

*Leaf shape.*—Linear to narrowly oblanceolate.

*Leaf division.*—Simple.

*Leaf base.*—Attenuate.

*Leaf apex.*—Acute with a blunt tip.

*Leaf venation.*—Pinnate, mid-rib on upper surface close to 198A, mid-rib on lower surface close to 194B, other veins match leaf coloration.

*Leaf margins.*—Revolute.

*Leaf arrangement.*—Opposite.

*Leaf attachment.*—Sessile.

*Leaf number.*—Average of 38 (19 pairs) per stem.

*Leaf surface.*—Upper surface and lower surface; moderately tomentose hairs about 0.2 mm in length and 192A to 192C in color.

*Leaf size.*—Average of 7 cm in length and 4 mm in width.

*Leaf internode length.*—Average of 8 mm in length.

*Leaf color.*—Young upper surface; close to 198A to 198B, young lower surface; 191C, mature upper and lower surface; 191A to 191B.

*Leaf fragrance.*—Strongly fragrant, typical *Lavandula* scent.

Inflorescence description:

*Inflorescence type.*—Conical spike with terminal verticillasters.

*Inflorescence number.*—1 Spike per flowering stem.

*Inflorescence fragrance.*—None.

*Lastingness of inflorescence.*—Average of 10 days.

*Inflorescence size.*—Average of 8.4 cm in height and 1.9 cm in width.

*Flower buds.*—Average of 5 mm in length and 2 mm in diameter, elliptic to oblong in shape, moderately pubescent, colour; 147D at base, 90B at apex.

*Flowers.*—Outward aspect, self-cleaning, salverform in shape, average of 1.2 cm in depth (height) and 6 mm in diameter, approximately 85 flowers per inflorescence, about 12 flowers per verticillaster.

*Petals.*—Dull and smooth on upper and lower surfaces, one upper lip with two identical lobes and one lower lip with three identical lobes, upper lip 4 mm in length, lower lip 2 mm in length, upper lip 4 mm in width, lower lip 6 mm in width, upper surface when fully open 90D in color, lower surface when fully open N88C in color, tube color; NN155C at base, N87D at distal end.

*Calyx.*—5 Sepals fused into a cylindrical tube, 5 mm in length and 2 mm in width, surface tomentose, color 193A at base and upper third close to 90A to 90C.

*Peduncles.*—Strong, average of 23.7 cm in length and 1.7 mm in diameter, aspect upright, surface 148A in colour with moderately tomentose hairs close to 157A to 157D in color.

*Pedicels.*—Moderately strong, average of 1 mm in length and 1 mm in diameter, and 147D in color.

*Flower bracts.*—Each whorl of flowers subtended by two bracts, broadly rhomboidal in shape, aristate apex, sessile, 5 mm in length and 5 mm in width, upper and lower surfaces 146B in color with veins close to 146A.

Reproductive organs:

*Pistils.*—1, pistil; 4 mm in length, stigma; narrow, club-shaped and 90C in color, style; 3 mm in length, NN155A in color, ovary; 144A in color.

*Stamens.*—4, anthers; dorsifixed, kidney-shaped, average of 0.5 mm in length, N155C in color, filament; implanted in petal, 2 mm in length, 84D in color, pollen; moderate in quantity, 21B in color.

*Fruit and seeds.*—No fruit or seed development has been observed.

It is claimed:

1. A new and distinct cultivar of *Lavandula* plant named 'LA007' as herein illustrated and described.

* * * * *